(12) United States Patent
Shapiro et al.

(10) Patent No.: US 10,610,344 B2
(45) Date of Patent: Apr. 7, 2020

(54) STRESS URINARY INCONTINENCE TREATMENT DEVICE, METHOD AND TOOLS

(71) Applicant: Floelle Inc., Acton, MA (US)

(72) Inventors: Jerrold M. Shapiro, Acton, MA (US); Cheri A. Grantham, Willis, TX (US); Anthony Wong, Franklin, MA (US); Jon T. McIntyre, Newton, MA (US); Allison M. Waller, Blackstone, MA (US)

(73) Assignee: Floelle Inc., Acton, MA (US)

( * ) Notice: Subject to any disclaimer, the term of this patent is extended or adjusted under 35 U.S.C. 154(b) by 28 days.

(21) Appl. No.: 15/355,335

(22) Filed: Nov. 18, 2016

(65) Prior Publication Data

US 2017/0065391 A1  Mar. 9, 2017

Related U.S. Application Data

(63) Continuation-in-part of application No. PCT/US2015/031446, filed on May 18, 2015.
(Continued)

(51) Int. Cl.
*A61F 2/04* (2013.01)
*A61F 2/00* (2006.01)

(52) U.S. Cl.
CPC ............ *A61F 2/004* (2013.01); *A61F 2/0022* (2013.01); *A61F 2002/047* (2013.01)

(58) Field of Classification Search
CPC ... A61F 2002/047; A61F 2/0022; A61F 2/004
See application file for complete search history.

(56) References Cited

U.S. PATENT DOCUMENTS 4,784,651 A   11/1988  Hickey
6,027,442 A   2/2000   Von Iderstein
(Continued)

FOREIGN PATENT DOCUMENTS

WO   2013/144770 A3   10/2013

OTHER PUBLICATIONS

The International Search Report and the Written Opinion of the International Searching Authority dated Aug. 13, 2015 for PCT Application No. PCT/US2015/031446.
(Continued)

*Primary Examiner* — Christine H Matthews
(74) *Attorney, Agent, or Firm* — Brian M. Dingman; Dingman IP Law, PC

(57) ABSTRACT

A device for use within a woman's urethra for obstructing urine outflow when the pressure in the woman's abdomen is at or above a threshold pressure level (IAP1). The device also allows urine outflow when the intra-abdominal pressure is below the threshold pressure level (IAP1). The device includes a flexible tube that is configured to be inserted into a urethra, wherein the tube defines a lumen that has inlet and outlet openings. The tube is configured to receive, conduct and discharge urine. The tube is further configured such that the lumen is at least partially obstructed when the pressure on the urethra surrounding the tube at least meets the threshold pressure (IAP1), and the lumen is more open when the pressure on the urethra surrounding the tube is at a level below a second, lower, threshold pressure (IAP2).

17 Claims, 6 Drawing Sheets

Related U.S. Application Data

(60) Provisional application No. 62/000,090, filed on May 19, 2014.

(56) References Cited

U.S. PATENT DOCUMENTS

| | | | |
|---|---|---|---|
| 2006/0122709 A1* | 6/2006 | Devonec | A61F 2/04 623/23.66 |
| 2012/0053570 A1 | 3/2012 | Yugari et al. | |
| 2014/0128666 A1 | 5/2014 | Shapiro et al. | |

OTHER PUBLICATIONS

The International Preliminary Report on Patentability dated Dec. 1, 2016 for PCT Application No. PCT/US2015/031446.

\* cited by examiner

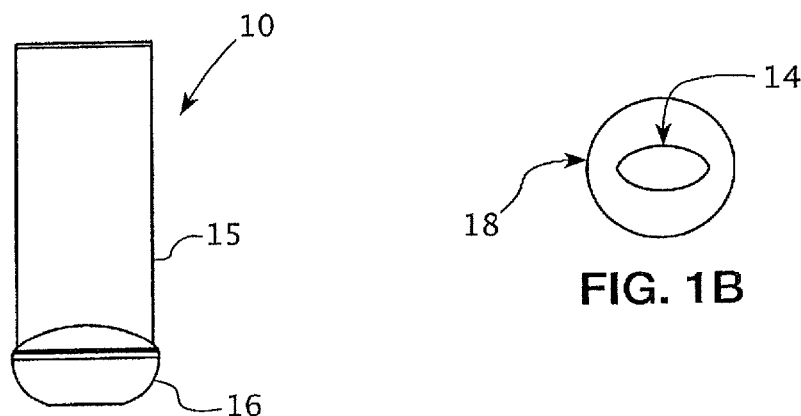
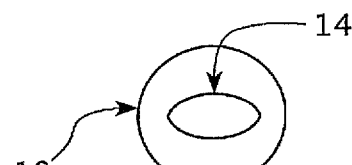
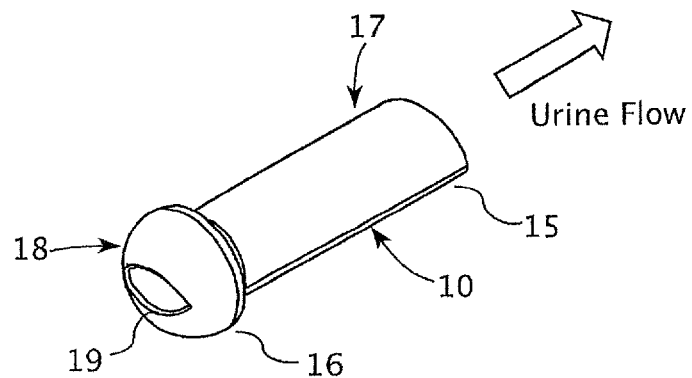
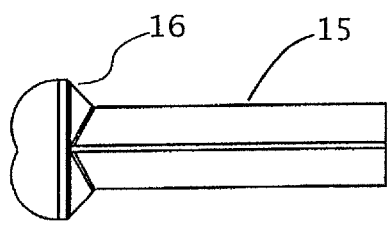
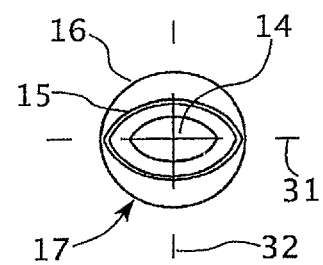

STRESS URINARY INCONTINENCE TREATMENT DEVICE, METHOD AND TOOLS

CROSS-REFERENCE TO RELATED APPLICATIONS

This application is a continuation in part of and claims priority from PCT/US15/31446, filed on May 18, 2015, which itself claimed priority from Provisional Application 62/000,090, filed on May 19, 2014.

BACKGROUND

This disclosure relates to devices for treating incontinence in human females, and in particular to devices that serve to inhibit or prevent the unwanted discharge of urine from the urinary tract.

Urinary incontinence, or involuntary urine outflow, affects sixteen percent of women in the United States of America. In about seventy five percent of these women, urinary incontinence occurs when the pressure in their abdomen, called the intra-abdominal pressure, or IAP, rises above a threshold pressure, called IAP1; this is called stress urinary incontinence. In about twenty percent of incontinent women, the detrusor muscle of the urinary bladder involuntarily contracts, producing a sudden urge to urinate; this is called urge urinary incontinence. Women with both stress and urge urinary incontinence are said to have mixed urinary incontinence.

While pharmaceutical treatment is available to relax the detrusor muscle and relieve urge urinary incontinence, there are no pharmaceuticals cleared by the U.S. Food and Drug Administration for treating stress urinary incontinence. Many surgical procedures have been developed to mechanically support the female urethra or to make it more rigid, but these are expensive, have side effects, often do not work and need to be repeated, and are chosen by few incontinent women. Devices to temporarily block urine flow using a urethral catheter whose proximal end expands inside the bladder need to be replaced every time the woman urinates, and are relatively expensive. Palliative measures, such as wearing an absorbent pad and changing it after every urination, are not only expensive but may leave the skin on the inner thighs wet, leading to abrasions and ulcers; while many pads contain deodorants, the residual urine odor is embarrassing for many incontinent women, leading to restricted social contacts and decreasing their quality of life.

It is thus desirable to provide a device to automatically control urinary discharge during sudden elevation of intra-abdominal pressure, which functions without intervention by the user and which does not impede her normal activities.

Prior art includes devices inserted through the female urethra into the bladder to seal the bladder neck until the devices are removed, and a device containing a manually operated drainage control valve that is inserted through the female urethra into the bladder.

SUMMARY

This disclosure relates to devices, methods and tools that are involved with controlling human female urinary incontinence without any purposeful intervention by the user, and more particularly to a female incontinence control device which obstructs urine outflow only when the woman coughs, sneezes, laughs, lifts or otherwise causes the pressure in her abdomen to rise above a threshold level, and allows normal urine outflow otherwise when the woman desires to urinate.

Disclosed herein is a device that automatically inhibits or prevents urinary discharge during elevation of intra-abdominal pressure, which functions without intervention by the user and which does not impede her normal activities.

Among the features of the disclosure may be noted the provision of a female incontinence device which is automatically activated by increased intra-abdominal pressure, a female incontinence device which is entirely contained within the body of the user, a female incontinence device which can be easily installed and removed, a female incontinence device which can be operationally fixed within the female urethra, a female incontinence device which effectively prevents urinary discharge when such discharge is not desired and permits such discharge when the user desires and the intra-abdominal pressure is less than a threshold pressure, a female incontinence device manufactured of materials which prevent the growth of bacteria on their surfaces, and a method for controlling female stress urinary incontinence and female mixed urinary incontinence.

Other features of the disclosure will be in part apparent and in part pointed out hereinafter. In accordance with the disclosure, the female incontinence device defines a passageway or lumen having inlet and outlet openings for receiving, conducting and discharging urine. The device is configured such that the lumen is obstructed when the pressure on the urethra surrounding it meets or exceeds a first threshold pressure (sometimes termed herein "IAP1"). The device is also configured such that the lumen defines a fluid path through the device when the pressure on the urethra surrounding it is below IAP1. In non-limiting examples the lumen opens when the IAP is at or below a second, lower threshold pressure (sometimes termed herein "IAP2").

In one embodiment, the device is located within the urethra and the device comprises a flexible, elastic tube. In use, the device is located such that at least some of the outer surface of the tube is in contact with the lining of the urethra. Intra-abdominal pressure elevations caused by, for example, coughing or sneezing, are transmitted through the urethra to this tube, causing the lumen within it to collapse and obstruct the flow of urine through the lumen. The tube can be made from an elastic material that returns to its initial inserted shape once intra-abdominal pressure returns to normal. The device thus serves as an elastic flow control valve that is normally open, but is automatically closed by a deformation of the valve due to increased intra-abdominal pressure, which typically results from the patient coughing, laughing, lifting, sneezing, and the like. The device thus inhibits or fully prevents involuntary urine leakage. The device may also include structure (such as a retaining ring) that holds the tube in a selected position within the urethra, ideally such that the proximal part of the device (closest to the urinary bladder) which is in contact with the lining of the urethra is also proximal to the part of the urethra that passes through the musculature of the pelvic floor, so that the musculature helps to retain the device in place in the urethra.

All examples and features mentioned below can be combined in any technically possible way.

Featured herein in one non-limiting example is a device for use within a woman's urethra for obstructing urine outflow when the pressure in the woman's abdomen rises at or above a threshold pressure level. The device allows urine outflow when the pressure in the woman's abdomen is lower than the threshold level, for example when the pressure is near the pressure when her abdominal muscles are relaxed.

The device includes a flexible tube that is configured to be inserted into the urethra, wherein the tube defines a lumen that has inlet and outlet openings. The tube is configured to receive, conduct and discharge urine. The tube is configured such that the lumen is fully or partially obstructed when the pressure on the urethra surrounding the tube meets or exceeds the threshold pressure. The lumen is more open when the pressure on the urethra surrounding the tube is at a level below the threshold pressure.

Embodiments may include one of the following features, or any combination thereof. The tube may comprise a material that is configured to return to its original shape after being deformed. The tube may be a hollow cylinder that may be generally in the shape of an elliptic cylinder. The lumen may define a cross-sectional shape that is generally biconvex lens-shaped, or generally elliptical-shaped. The tube may have a cross-sectional shape that is generally biconvex lens-shaped, or generally elliptical-shaped. The tube and the lumen may both have a major axis, where the two major axes are generally parallel or coincident. When the lumen is not constricted, its boundary may be in the shape of an ellipse, a circle, or an axial cross-section of a double-convex lens with sharp edges (hereinafter sometimes referred to as a "cat's eye" profile); other shapes of the tube and the lumen are possible and are contemplated herein.

Embodiments may include one of the following features, or any combination thereof. The lumen may be open when the pressure on the urethra surrounding the tube is at about 10 cm of water. The first threshold pressure where the lumen is constricted or closed may be about 100 cm of water. At an intra-abdominal pressure of about 10 cm of water, the lumen may be sufficiently open such that urine is able to flow through the lumen. The tube may have a variable wall thickness around a circumference of the tube. The tube may be configured to collapse at a pressure that is at least as great as the threshold pressure level. The device may comprise a material that is configured to kill bacteria, or inhibit growth of bacteria that come in contact with the device.

Embodiments may include one of the following features, or any combination thereof. The device may further comprise a retaining ring or another anti-migration feature disposed on the outside of the tube. The retaining ring may be disposed on a proximal end of the tube. The tube and the retaining ring may be unitary. The circumference of the retaining ring may be at least about 18 French. The retaining ring may be separate from the tube, and it may be more rigid than the tube. The retaining ring may comprise an inflatable structure coupled to the outside of the tube, and configured to be filled with a fluid in situ, so as to expand the retaining ring. The retaining ring may include within it a more rigid material, such as medical grade stainless steel. The retaining ring or other antimigration feature may be a separate structure that is coupled to the outside of the tubular section, or it may be formed of the same material and/or integral with the tubular section. The retaining ring/antimigration feature is preferably but not necessarily located on the proximal part of the tubular section.

Featured herein in another non-limiting example is a method for inhibiting urine outflow in a female, comprising locating a device in the female's urethra, wherein the device comprises a flexible tube that defines a lumen that has inlet and outlet openings, the tube configured to receive, conduct and discharge urine. The tube is configured such that the lumen is fully or partially obstructed when the pressure on the urethra surrounding the tube meets or exceeds a threshold pressure, and the lumen is more open when the pressure on the urethra surrounding the tube is at a level below the threshold pressure.

Embodiments may include one of the following features, or any combination thereof. The method may further comprise delivering the device to the urethra through a sheath. The device may be deployed from the sheath into the urethra using an insertion tool that is configured to engage and be released from the device. The insertion tool may (or may not) be further configured to remove the device from the urethra.

Featured herein in another non-limiting example is a tool kit comprising a tool that is configured to insert into a female urethra, a device that comprises a flexible tube that defines a lumen that has inlet and outlet openings. The tube is configured to receive, conduct and discharge urine. The tube is further configured such that the lumen is fully or partially obstructed when the pressure on the urethra surrounding the tube meets or exceeds a threshold pressure, and the lumen is more open when the pressure on the urethra surrounding the tube is at a level below the threshold pressure.

Embodiments may include one of the following features, or any combination thereof. The tool may comprise a sheath that carries the device within the sheath. The tool may further comprise a push rod that is configured to move within the sheath, to push the device out of the sheath. The push rod may be further configured to engage the device while the device is located in the urethra such that the device can be removed from the urethra using the push rod. The push rod may comprise a tip that is configured to pass through the device lumen. The tip may further comprise an expansion mechanism that is configured to be selectively expanded such that a largest dimension of the cross-section of the expansion mechanism is greater than the largest dimension of the lumen. The tool kit may further comprise a tool that is configured to remove the device from the urethra. The tool that is configured to remove the device from the urethra may comprise an inflatable structure that is configured to be passed through the device lumen and be inflated to a size that is larger than the lumen, such that the inflatable structure can be used to pull the device out of the urethra.

BRIEF DESCRIPTION OF THE DRAWINGS

FIGS. 1A, 1B, 1C, 1D and 1E are top, proximal end, side, perspective and distal end views, respectively, of an embodiment of a device that is configured to inhibit stress urinary incontinence in human females.

DETAILED DESCRIPTION

Figure 2:
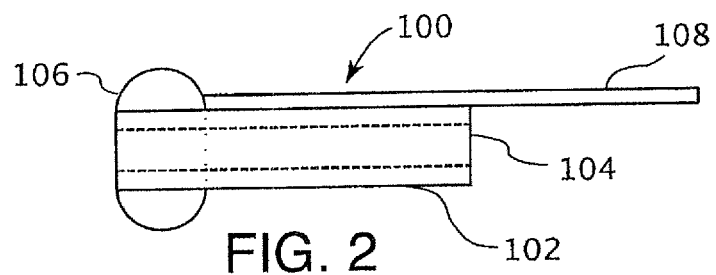
FIG. 2 shows another example of a device that is configured to inhibit stress urinary incontinence in human females.

FIGS. 1A-1E show one embodiment of a device 10 that is configured to inhibit or prevent stress urinary incontinence in a human female. Device 10 may also be used in non-human females, with appropriate modifications of sizes, device design and materials as needed, as would be apparent to one skilled in the technical field given the anatomy and the likely IAP levels in the species. Device 10 comprises a flexible elastic tube 15, and a retaining ring (or other device retention feature) 16 that has a larger diameter than tube 15. Tube 15 is configured to be inserted into a urethra. Tube 15 has a lumen with inlet and outlet openings for receiving, conducting and discharging urinary fluid. Tube 15 is configured such that the lumen is fully or partially obstructed when the pressure on the urethra surrounding the tube meets or exceeds a first threshold pressure (IAP1), and such that the lumen is more open when the pressure on the urethra surrounding the tube is at a level below this first threshold pressure. Tube 15 and ring 16 are connected (in one example, they are integral portions of a unitary molded structure) to form a structure. Device 10 can be manufactured as a single piece, or it can be a multi-piece construction. Retaining ring 16 preferably has a circumference that is about as large as or just larger than the circumference of the urethra; this can be but need not be about 18 French (which corresponds to a round tube with a diameter of 6 mm). Retaining ring 16 is constructed and arranged to maintain the location of the device along the long axis of the female urethra. Retaining ring 16 may be separate from tube 15 and made of a material that is more rigid than the tube.

The cross section of the outside of tube 15 is preferably but not necessarily an ellipse, including the case where the major and minor axes of the ellipse are of equal length, commonly known as a circle. Tube 15 may thus be considered to be a hollow cylinder, preferably but not necessarily an elliptic cylinder. The wall thickness of tube 15 may be consistent around its circumference (as shown in FIG. 1E), or it may not be, as further described below. Tube 15 and/or its lumen may have a cat's eye cross-sectional shape, or a different shape such as elliptical. The tube and its lumen may both have a major axis 31, and a minor axis 32. Major axes 31 and/or minor axes 32 may be coincident, or may be parallel, or not. In one non-limiting example, the dimensions of device 10 may be as follows: overall length 19 mm, width of tube 6.7 mm, height of tube 4.3 mm, height of lumen 2.3 mm, width of lumen 4.5 mm, length of retaining ring 2.9 mm, diameter of retaining ring 7.3 mm.

The distal end 17 (nearest the vulva when the device is inside the female urethra) in this embodiment is toward the upper right of FIG. 1D. The proximal end 18 (nearest the urinary bladder when the device is inside the female urethra) in this embodiment is toward the lower left of FIG. 1D. The circumference of the outside of tube 15 can be (but need not be) approximately equal to or just less than the circumference of the inside of the human adult female urethra. Various models with different tube diameters and/or retaining ring diameters may be designed so as to properly fit different women.

Device 10 is meant to be placed in the mid-urethra of a woman. Device 10 should lie entirely within the urethra. Preferably but not necessarily retaining ring/device retention feature 16 is proximal to the part of the urethra that passes through the musculature of the pelvic floor, so that this musculature helps to retain device 10 in the urethra. When so placed, when her intra-abdominal pressure, abbreviated IAP, is low, the device will be generally tubular in shape, with lumen 14 open. When the woman initiates the micturition reflex, her bladder's detrusor muscles contract. This causes urine to flow from her bladder through her urethra and through the lumen 14 that is located along the longitudinal axis of device 10, and exit outside her body. Tube 15 has a central entrance opening 19 to the device (i.e., the opening of lumen 14), into which urine flows from the bladder. The fluid pressure of her urine against the inner wall of tube 15 pushes the inner portions of this tube away from the device's longitudinal axis. This, along with the elasticity of the material from which tube 15 is made, creates a full-length lumen or passageway 14 for urine flow.

When the woman is not micturating, but raises her IAP by coughing, laughing, sneezing, jogging, lifting or other means, the increased IAP presses her urethra against the outer surfaces of the tube 15. This collapses the flexible tube, thereby occluding the device lumen 14 where it passes through the distal part of the device, thus blocking urine flow through the device. Once the IAP returns to normal, the flexible, elastic tube returns to its original shape and allows urine flow during micturition.

In illustrative but non-limiting examples, IAP1 (the pressure which causes the lumen to collapse) is about 100 cm of water. IAP1 can have different levels depending on the person, the body makeup and other factors. It is believed but not required that IAP1 is likely to be in the range of from about 50 to about 100 cm of water. The device and its tube can be configured such that the lumen collapses at a design IAP1. Relevant tube design parameters include but are not limited to: material, wall thickness, wall cross-sectional shape and lumen cross-sectional shape. IAP2 (the lower pressure where the lumen reopens after having been closed) is preferably but not necessarily designed to be a normal IAP. This depends on whether the woman is standing, sitting or lying down, whether she is thin, average or obese, etc. IAP2 is believed to be anywhere from about 10 to about 40 cm of water. This disclosure, however, is specifically not limited by any values of IAP1 or IAP2.

Device 10 can be constructed of a material that returns to its original shape after being deformed by the increased IAP. The material(s) may be biocompatible materials such as polydimethylsiloxane (PDMS), a silicone rubber, or alternatives like thermoplastic polyurethanes made by Bayer, such as Texin and Desmopan or other elastomers. Tube 15 along some or all of its length needs to have sufficient elasticity that it returns to its original shape after having been deformed. The more rigid parts of the device if present (e.g., the retaining ring) can be machined or molded from a biocompatible plastic such as polyetheretherketone (e.g., Zeniva PEEK from Solvay Advanced Polymers LLC in Alpharetta, Ga., USA) with polysulfone, polyphenylsulfone, ABS, high density polyethylene or polyetherimide as alternative biocompatible plastics.

Ionic silver in a zeolite carrier from Agion Technologies, a brand of Sciessent LLC in Wakefield, Mass., USA, or equivalent antimicrobial compounds, can be incorporated into these flexible and more rigid materials to give them antimicrobial properties. Patterns may also be constructed on all surfaces of the device which prevent bacteria from adhering to such surfaces and thereby prevent the formation of biofilms, such as those produced by Sharklet Technologies Inc. of Aurora, Colo., USA, or other such patterns and surface finishes. To inhibit or prevent the growth of microbes on the surfaces of the device, an antimicrobial substance can be mixed or compounded into the materials before they are formed into the parts of the device. To inhibit or prevent urine crystals, if any, from adhering to the device all surfaces of the device in contact with urine can be coated with a highly lubricious material, such as a hydrophilic material, polytetrafluoroethylene (PTFE), parylene, polyvinylpyrrolidone-polyurethane interpolymers, or Lubri-LAST™ (AST Products, Billerica Mass., USA).

Alternative embodiments of the tube include those with an oval outside diameter, and those with an inside diameter that includes geometric features that facilitate closure during an increase in IAP such as an ellipse or cat's eye profile. Also, the retaining ring may be made from a rigid or compliant material.

The retaining ring may have a radial cross-section which is flat on the surface in contact with the tube and round on the surface in contact with the female urethral lining so as to inhibit or prevent damage to and/or erosion of such urethral lining. The retaining ring may be constructed of a single material, preferably a soft material. Alternatively, as shown by alternative device 100, FIG. 2, retaining ring 106 may be constructed as a flexible outer shell with an inner filling of a liquid such as distilled water, or another biocompatible fluid. If such retaining ring 106 is to be filled with a liquid, a means for filling ring 106 with liquid, in situ, and draining the fluid from the ring (so that the device may be removed from the urethra) may be provided. For example, fluid conduit 108 may be used to add fluid to and withdraw fluid from the inside of ring 106. Device 100 includes elastic tube 102 with lumen 104, which may be the same as tube 15 and its lumen 14 of device 10, FIG. 1. In one example, the device can be molded from a soft material such as a silicone rubber with a 10 durometer on the Shore A scale. The softness of this material means that the retaining ring might become twisted upon insertion, in which case it might not seat properly in the urethra. Additional stiffness and integrity may be provided by reinforcing the retaining ring. One manner in which the retaining ring could be reinforced would be to insert mold a medical grade stainless steel ring, 148, into the retaining ring. The steel ring could also serve as an anchor point for the loop of suture material, 142, that can be included to facilitate removal of the device from the urethra, as is explained below.

Figures 3A, 3B, 3C:
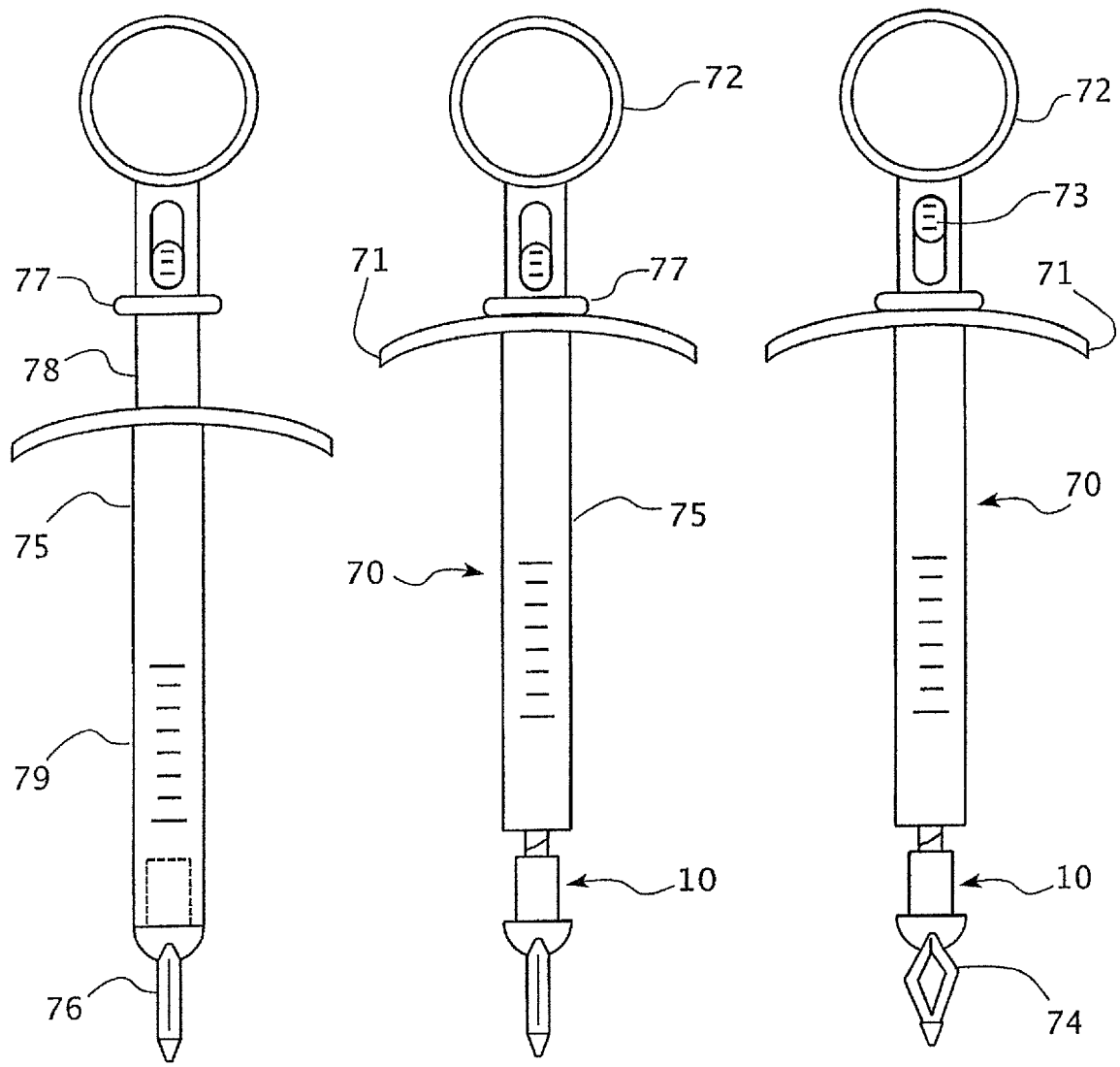
FIGS. 3A, 3B and 3C are side views of an embodiment of a tool that can be used to insert the device of FIG. 1 into, and remove such device from, the urethra of human females.

FIGS. 3A-3C shows one embodiment of a tool 70 that can be used to insert the device 10 into, and remove such device from, the urethra of human females. Tool 70 may be part of or may comprise a tool kit for inserting the device into and removing the device from the urethra. The insertion/removal tool 70 consists of a hollow tube or sheath 75 containing a push rod 78 which can move along its long axis within sheath 75, a graduated insertion depth scale 79, a ring 72 for advancing and withdrawing push rod 78 within sheath 75, a tip 76 of the pushrod 78 containing an expansion mechanism 74, a stop 77, a finger grip 71, and a mechanism 73 for operating the expansion mechanism 74. FIG. 3A shows the device 10 inserted into the sheath 75 with the tip 76 passing within and extending from the device 10. The device 10, held within tool 70, is inserted into the human female urethra until a mark on the graduated scale 79 is adjacent to her urethral meatus. The length of the corresponding urethra, measured separately, corresponds to one of the marks on the graduated scale 79. The marks are located such that once the insertion process is completed the device 10 will be centered along the length of her urethra (or placed in another location in the urethra, as desired or as necessary). FIG. 3B shows the device 10 after the sheath 75 is withdrawn while the ring 72 is held still with respect to the woman's body until the stop 77 is touching the finger grip 71. Not shown are the human female urethra and its sticky endothelial mucosa holding the device 10 in place while the sheath 75 is withdrawn. Once finger grip 71 touches stop 77, the insertion/removal device 75 can be completely removed from the urethra.

In order to remove the device 10 from the female urethra, tool 70 is inserted into the urethra and tip 76 is inserted into the lumen of device 10 until pushrod 78 touches the device's proximal end and further insertion is resisted. FIG. 3B also shows the relative positions of device 10 and tool 70 after tool 70 has been inserted into the urethra and through the lumen of device 10 just prior to removing such device from the urethra. The expansion mechanism 74 is then deployed to lock the device 10 between the pushrod 78 and itself, 74. FIG. 3C shows the mechanism 73 moved towards the ring 72 so as to cause expansion of the expansion mechanism 74; this engages the device 10 with the pushrod 78 so that withdrawal of the tool 70 from the urethra will remove device 10 from the urethra.

Figure 4:
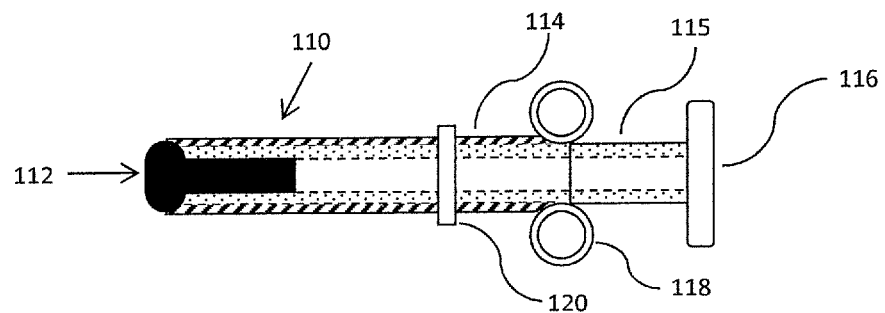
FIG. 4 shows another example of a tool that can be used to insert the device that is configured to inhibit stress urinary incontinence in human females into the urethra of human females.

More generally and as shown in FIG. 4, a tool 110 for inserting into the female urethra a device 112 which is similar to device 10. Device 112 is configured to inhibit or prevent stress urinary incontinence in a human female. Tool 110 may include a hollow cylinder 114 (preferably but not necessarily of round or elliptical cross-section) into which the device 112 is loaded, an indication such as markings (not shown) on the outside of such cylinder 114 of the distance between such indication and the end of the cylinder that will be closest to the woman's bladder. There is also a plunger 115 (e.g., a hollow cylinder with an elliptical cross-section that can act as a pushrod) that fits into and can slide within the hollow cylinder 114, and fits over the stein of device 112 so as to rest against the retaining ring of device 112. There are also means, such as stop 120, for holding the indication adjacent to the female urethral meatus while the plunger is pushed via end 116 into the cylinder to expel the device, and a means, such as bilateral finger grips 118, for use in withdrawing the cylinder from the female urethra. As the hollow cylinder 114 introduces the device into the female urethra, it may be called an introducer sheath. The introducer sheath may be made of or its inside may be coated with a slippery material such as Teflon® to reduce the friction force between the device and the inside of such sheath.

Figure 5:
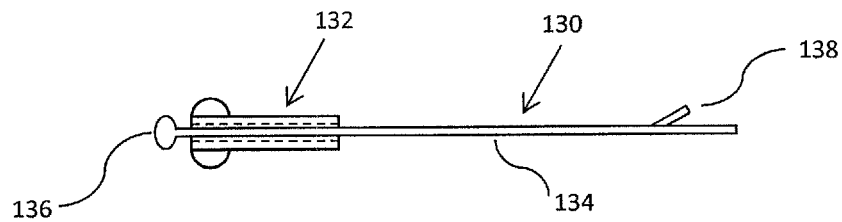
FIG. 5 shows an example of a tool that can be used to remove the device that is configured to inhibit stress urinary incontinence in human females from the urethra of human females.

A different tool 130, FIG. 5, may be used to remove from the female urethra a device 132 which is similar to device 10. Device 132 is configured to inhibit or prevent stress urinary incontinence in a human female. Tool 130 may consist of a hollow tube 134 with a balloon 136 at its far end. With the balloon 136 deflated, tube 134 is inserted into the urethra and into the lumen in device 132 until balloon 136 is on the other (facing the patient's bladder) side of device 132. The balloon 136 is then inflated with a liquid or gas via inlet 138 so that its outside diameter is greater than the largest dimension of the lumen of device 132. Tube 134 is then pulled away from the patient's body, withdrawing the device 132 with it.

Figure 6:
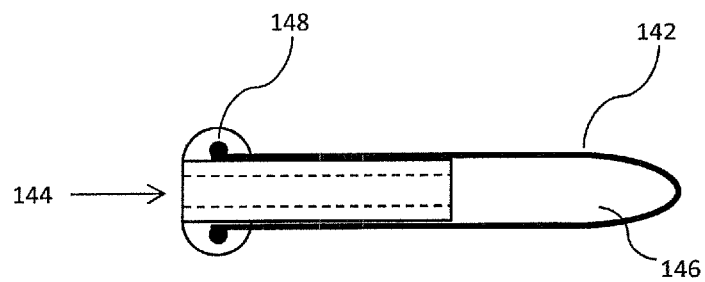
FIG. 6 shows an example of a construction of a device that is configured to inhibit stress urinary incontinence in human females that facilitates removal of the device from the urethra.
Figure 7A:
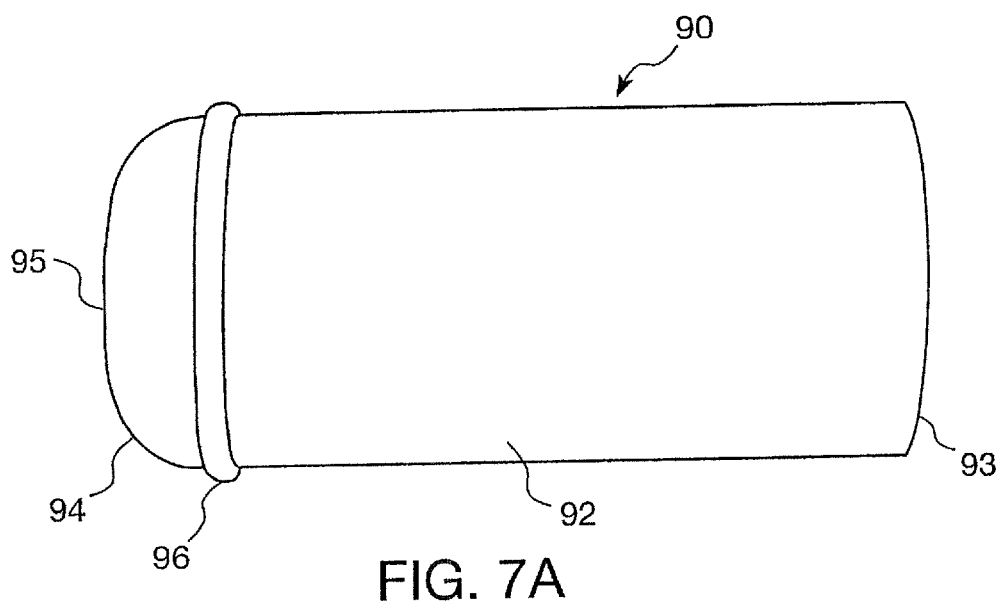
FIGS. 7A-7D are side, perspective, proximal end and distal end views, respectively, of another embodiment of a device that is configured to inhibit stress urinary incontinence in human females.
Figure 7B:
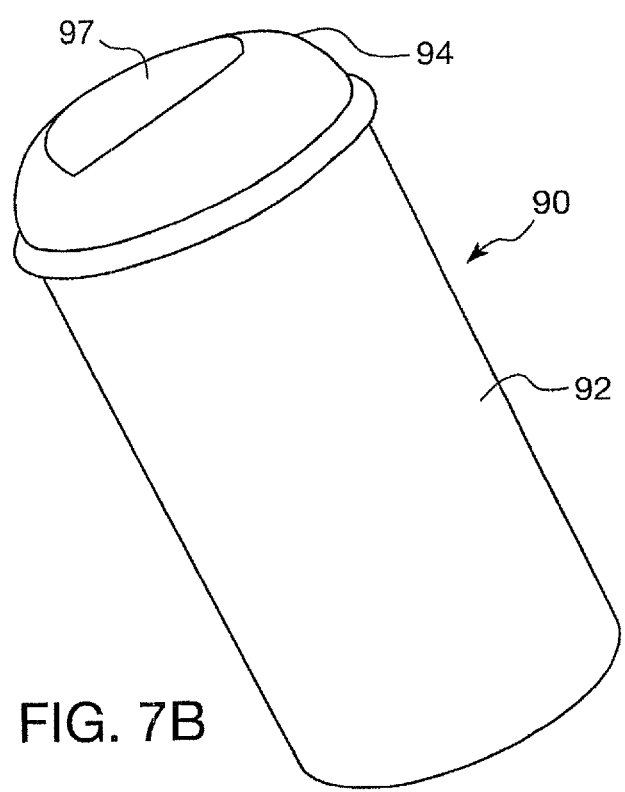
Figure 7C:
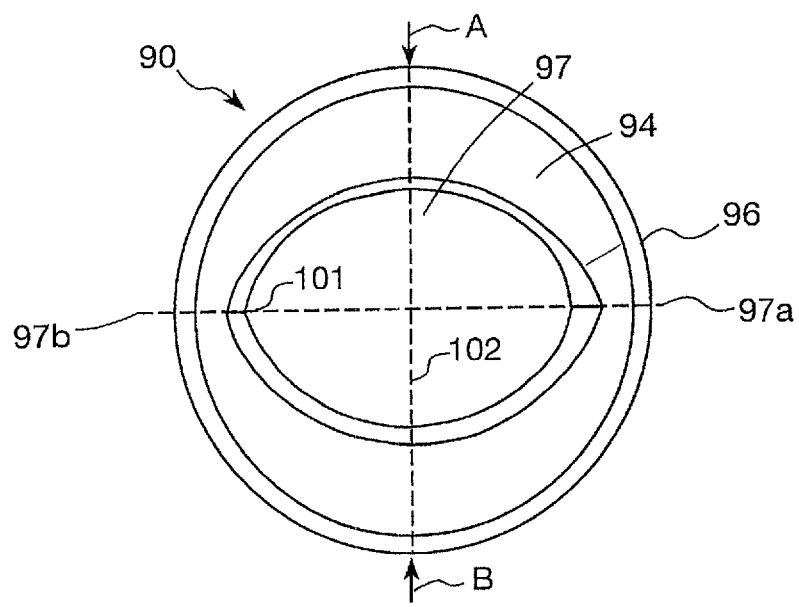
Figure 7D:
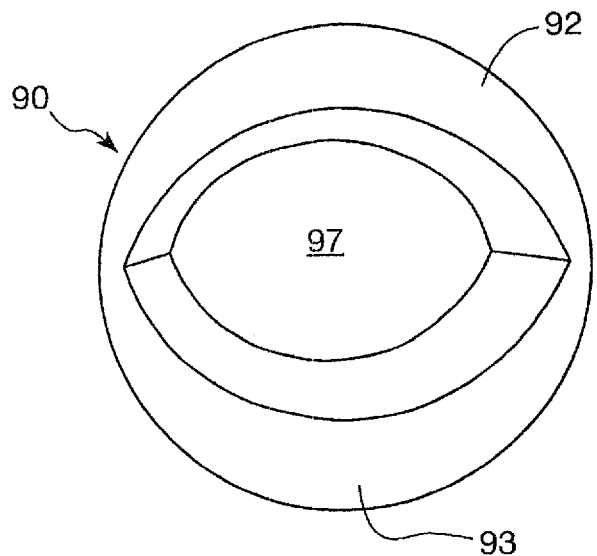

Alternatively or additionally and as shown in FIG. 6, a loop 142 of biocompatible material may be fixed (e.g., glued) to) to the distal end of device 144 which is similar to device 10. Device 144 is configured to inhibit or prevent stress urinary incontinence in a human female. Loop 142 facilitates removing device 144 by inserting a tool (not shown)

into the female urethra to engage this loop (e.g., using a hook that engages in space 146 behind loop 142) and using such tool to pull the device 144 out of the urethra. Loop 142 may be engaged with the steel ring that is in the retaining ring of the device. Loop 142 may be made from a suture material, and may extend to about 10 mm distal to the device so it can be grasped and used to pull the device out of the urethra.

FIGS. 7A-7D illustrate another arrangement of the disclosed device. Device 90 is configured to inhibit or prevent stress urinary incontinence in a human female. Device 90 comprises tube 92 that has central lumen 97 with the urine inlet opening in proximal end 95 and outlet opening in distal end 93. Proximal end 95 can include a domed end portion 94 to facilitate insertion of the device into the female urethra. As can be seen in the end views, lumen 97 is generally shaped as a biconvex lens with sharp edges. Alternatively, the lumen may be more elliptical-shaped. Since tube 92 is round or elliptical, the lumen creates thinner wall portions at locations 97a and 97b (along the major axis 101 of lumen 97) as compared to the thicker wall portions along the minor axis 102 of lumen 97. This construction causes the tube to preferentially collapse toward major axis 101 (along arrows A and B, FIG. 7C) when inward pressure is applied around the circumference of tube 92. Projection 96 (which in this case is like an integral O-ring) accomplishes a greater diameter near the proximal end that creates a tight fit with the urethra, to help hold or retain the device in place in the urethra. Projection 96 could alternatively be a separate piece that is affixed to the tube.

Figure 8:
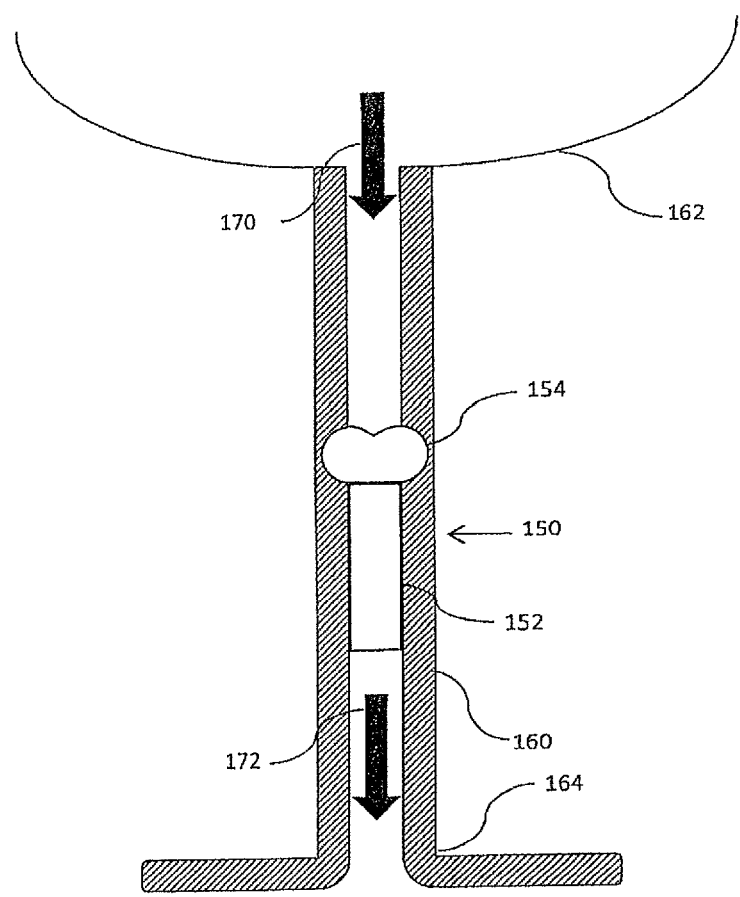
FIG. 8 shows an example of a device that is configured to inhibit stress urinary incontinence in human females, in place in the urethra.

FIG. 8 shows device 150 that is configured to inhibit or prevent stress urinary incontinence in a human female in place in urethra 160 that leads from bladder 162 to urethral meatus 164. Device 150 has retaining feature 154 that indents the urethral wall, and tube 152 that sits close to or against the urethral wall. Urine flows in the direction of arrows 170 and 172. When IAP increases to IAP1, tube 152 collapses as described above. When IAP subsequently decreases below IAP1 (e.g., to a normal level (IAP2)), tube 152 reopens to allow the flow of urine.

A number of implementations have been described. Nevertheless, it will be understood that additional modifications may be made without departing from the scope of the inventive concepts described herein, and, accordingly, other embodiments are within the scope of the following claims.

What is claimed is:

1. A device for use within a female urethra for selectively obstructing urine outflow and also allowing urine outflow, the device comprising:
    a solid flexible tube that is configured to be inserted into the urethra, wherein the tube defines a lumen that has inlet and outlet openings, the tube configured to receive, conduct and discharge urine, wherein the tube has a biconvex lens-shaped cross-section, and wherein the linen defines a biconvex lens-shaped cross-section;
    wherein the tube is configured such that the tube collapses such that its lumen is at least partially obstructed when a pressure on, the urethra surrounding the tube at least meets a threshold pressure, and the lumen is more open when the pressure on the urethra surrounding the tube is at a level below the threshold pressure.

2. The device of claim 1, wherein the tube is unitary and is made entirely from a material that is configured to return to its original shape after being deformed.

3. The device of claim 1 wherein the tube and the lumen both have a major axis, and where the two major axes are coincident.

4. The device of claim 1 wherein the lumen is open when the pressure on the urethra surrounding the tube is at about 10 cm of water.

5. The device of claim 4 wherein the threshold pressure is about 100 cm of water.

6. The device of claim 1 wherein at an intra-abdominal pressure of about 10 cm of water or less, the lumen is sufficiently open such that urine is able to flow therethrough.

7. The device of claim 1 further comprising a retention feature disposed on an outside of the tube.

8. The device of claim 7 wherein the retention feature comprises a retaining ring that is disposed on a proximal end of the tube.

9. The device of claim 8 wherein the tube and the retaining ring are unitary.

10. The device of claim 7 wherein the retention feature comprises a retaining ring with a circumference of at least about 18 French.

11. The device of claim 7, wherein the retention feature is separate from the tube, and is more rigid than the tube.

12. The device of claim 7 wherein the retention feature comprises an inflatable structure coupled to the outside of the tube, and configured to be filled with a fluid in situ, so as to expand the retention feature.

13. The device of claim 1 wherein the tube has a variable wall thickness around a circumference of the tube.

14. The device of claim 13 wherein the tube is configured to collapse at a pressure that is at least as great as the threshold pressure level.

15. The device of claim 1 comprising a material that is configured to at least one of kill bacteria and inhibit growth of bacteria that come in contact with the device.

16. A device for use within a female urethra for selectively obstructing urine outflow and also allowing urine outflow, the device comprising:
    a solid flexible tube that is configured to be inserted into the urethra, wherein the tube defines a lumen that has inlet and outlet openings, the tube configured to receive, conduct and discharge urine;
    wherein the tube is configured such that the tube collapses such that its lumen is at least partially obstructed when a pressure on the urethra surrounding the tube at least meets a threshold pressure, and the lumen is more open when the pressure on the urethra surrounding the tube is at a level below the threshold pressure; and
    a retention feature disposed on an outside of the tube, wherein the retention feature comprises a retaining ring with a circumference of at least about 18 French.

17. A device for use within a female urethra for selectively obstructing urine outflow and also allowing urine outflow, the device comprising:
    a solid flexible tube that is configured to be inserted into the urethra, wherein the tube defines a lumen that has inlet and outlet openings, the tube configured to receive, conduct and discharge urine;
    wherein the tube is configured such that the tube collapses such that its lumen is at least partially obstructed when a pressure on the urethra surrounding the tube at least meets a threshold pressure, and the lumen is more open when the pressure on the urethra surrounding the tube is at a level below the threshold pressure; and
    a retention feature disposed on an outside of the tube, wherein the retention feature is separate from the tube and is more rigid than the tube.

* * * * *